United States Patent
Vicario et al.

(10) Patent No.: US 11,844,610 B2
(45) Date of Patent: Dec. 19, 2023

(54) SYSTEM AND METHOD FOR MONITORING GAS EXCHANGE

(71) Applicant: KONINKLIJKE PHILIPS N.V., Eindhoven (NL)

(72) Inventors: Francesco Vicario, Boston, MA (US); William Anthony Truschel, Monroeville, PA (US); Pablo Andres Nanez Ojeda, Monroeville, PA (US); Michael Polkey, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 561 days.

(21) Appl. No.: 17/120,620

(22) Filed: Dec. 14, 2020

(65) Prior Publication Data

US 2021/0186387 A1 Jun. 24, 2021

Related U.S. Application Data (60) Provisional application No. 62/952,523, filed on Dec. 23, 2019.

(51) Int. Cl.
| | |
|---|---|
| *A61B 5/00* | (2006.01) |
| *A61B 5/145* | (2006.01) |
| *A61B 5/024* | (2006.01) |
| *A61B 5/085* | (2006.01) |
| *A61B 5/091* | (2006.01) |

(52) U.S. Cl.
CPC .......... *A61B 5/14542* (2013.01); *A61B 5/024* (2013.01); *A61B 5/085* (2013.01); *A61B 5/091* (2013.01); *A61B 5/4806* (2013.01); *A61B 5/4836* (2013.01); *A61B 5/4842* (2013.01)

(58) Field of Classification Search
CPC ..... A61B 5/14542; A61B 5/024; A61B 5/085; A61B 5/091; A61B 5/4806; A61B 5/4836; A61B 5/4842
See application file for complete search history.

(56) References Cited

U.S. PATENT DOCUMENTS

| | | |
|---|---|---|
| 6,258,038 B1 | 7/2001 | Haryadi et al. |
| 7,810,497 B2 | 10/2010 | Blake |
| 8,460,202 B2 | 6/2013 | Fisher et al. |
| 9,173,595 B2 | 11/2015 | Tusman et al. |

(Continued)

FOREIGN PATENT DOCUMENTS

WO  WO/2018/185714  * 10/2018  ............. A61B 5/082

OTHER PUBLICATIONS

International Search Report for PCT/EP2020/087831 filed Dec. 23, 2020.

*Primary Examiner* — Steven O Douglas
(74) *Attorney, Agent, or Firm* — Daniel H. Brean (57) ABSTRACT

The present disclosure pertains to a system and method for monitoring lung disease in a patient that is based on information that is derivable from home therapy devices including a ventilation therapy device and an oxygen saturation monitor such as a pulse oximeter. The measured parameters are used to model shunt fraction and a volume of dead space. Based on changes in gas exchange and results of a nitrogen washout test, a change in gas exchange impairment in the patient is observed and is then used to determine progression of a disease, identify a cause of the impairment, and/or to guide treatment of the patient.

15 Claims, 8 Drawing Sheets

(56) References Cited

U.S. PATENT DOCUMENTS

| | | |
|---|---|---|
| 9,655,544 B2 | 5/2017 | Stenqvist |
| 2002/0120207 A1 | 8/2002 | Hoffman |
| 2008/0221460 A1 | 9/2008 | Bae et al. |
| 2016/0100808 A1* | 4/2016 | Anbarani ............. A61B 5/7282 |
| | | 600/536 |
| 2018/0153440 A1 | 6/2018 | Lee et al. |
| 2019/0200941 A1 | 7/2019 | Chandran |
| 2020/0327993 A1 | 10/2020 | Jensen |
| 2021/0138172 A1 | 5/2021 | Assi |
| 2022/0401676 A1* | 12/2022 | Payton ................. A61M 16/12 |

* cited by examiner

SYSTEM AND METHOD FOR MONITORING GAS EXCHANGE

CROSS-REFERENCE TO RELATED APPLICATIONS

This patent application claims the priority benefit under 35 U.S.C. § 119(e) of U.S. Provisional Application No. 62/952,523, filed on Dec. 23, 2019, the contents of which are herein incorporated by reference.

BACKGROUND

1. Field

The present disclosure pertains to a system and method for monitoring progression of patients with lung disease, and more particularly to a system and method for monitoring gas exchange impairment.

2. Description of the Related Art

Chronic obstructive pulmonary disease (COPD) is a progressive disease characterized by the loss of parenchymal tissue (i.e., tissue essential to lung function) due to emphysema (i.e., damage to the air sacs in the lungs). As a result, the structure of the lungs in COPD changes over time. This has detrimental consequences on the ability of the cardiovascular system to transfer oxygen from inhaled air into the blood for transport to tissues. More specifically, the structural changes in the lungs cause inhomogeneous ventilation perfusion imbalance. Some regions of the lungs are ventilated but not adequately perfused; others are perfused but not adequately ventilated. Wasted ventilation and wasted perfusion reduce the overall gas exchange efficiency in COPD, leading to hypoxemia.

Given the progressive nature of COPD, monitoring is essential to timely capture the need for interventions, from improving patient compliance with medical and physical therapies, to changing prescriptions and/or escalating treatment.

Pulmonary function testing can be difficult to administer in a home health environment, and may also be uncomfortable for a patient to undergo. Machinery to monitor lung and cardiovascular performance may be bulky and/or expensive. These and other drawbacks exist.

SUMMARY

Accordingly, one or more aspects of the present disclosure relate to a system for a ventilation therapy device configured to provide ventilation therapy to the patient and to determine tidal volumes, flow of gas, and applied pressure provided to the patient, the ventilation therapy device including a blender configured and arranged to control a fraction of inhaled oxygen to perform a nitrogen washout test, an oxygen saturation monitor, configured to determine a saturation of oxygen in the patient's blood, a processor configured by machine-readable instructions to control the ventilation therapy device to perform the nitrogen washout test, determine, based on a result of the nitrogen washout test and the determined saturation of oxygen in the patient's blood, a change in gas exchange impairment in the patient, and determine, based at least in part on the result of the nitrogen washout test and the determined saturation of oxygen in the patient's blood, a cause of the change in gas exchange impairment in the patient.

One or more aspects relate to a method of monitoring lung disease in a patient including providing ventilation therapy using a ventilation therapy device to the patient, determining tidal volumes, flow of gas, and applied pressure provided to the patient using the ventilation therapy device, determining a saturation of oxygen in the patient's blood, controlling the ventilation therapy device to perform a nitrogen washout test, determining, based on a result of the nitrogen washout test and the determined saturation of oxygen in the patient's blood, a change in gas exchange impairment in the patient, and determining, based at least in part on the result of the nitrogen washout test and the determined saturation of oxygen in the patient's blood, a cause of the change in gas exchange impairment in the patient.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

COPD is best understood as a group of diseases in which the patient suffers from some degree of breathing impairment due to blockages in airways. The impairment may involve ventilation (flow of air) or respiration (exchange of gases between the lung and the blood). Often a variety of pathologies will be present in a patient, and may include most commonly emphysema (damage to the alveoli) and chronic bronchitis (inflammation of the bronchial tubes leading to mucus production, coughing and difficulty breathing). Exacerbations, or acute sever symptoms, both require additional care during an event and tend to cause longer term damage such that a patient who undergoes an exacerbation is more likely to experience them again in the future.

Non-invasive ventilation (ventilation using a mask rather than tracheal intubation) is one of the basic treatments and has been found to be effective in reducing mortality rates and rehospitalization in COPD patients. Devices for home health non-invasive ventilation include BiPAP devices, for example. Though in some sense not technically a non-invasive ventilation device, for the purposes of this disclosure, CPAP may also be considered to constitute non-invasive ventilation.

In accordance with an embodiment, the ventilator itself may be used to assist in not just treating the symptoms, but further in monitoring progression of the disease. Furthermore, in an embodiment, the same system may be used to provide information regarding comorbidities, and distinguishing various comorbidities from each other.

Figure 1:
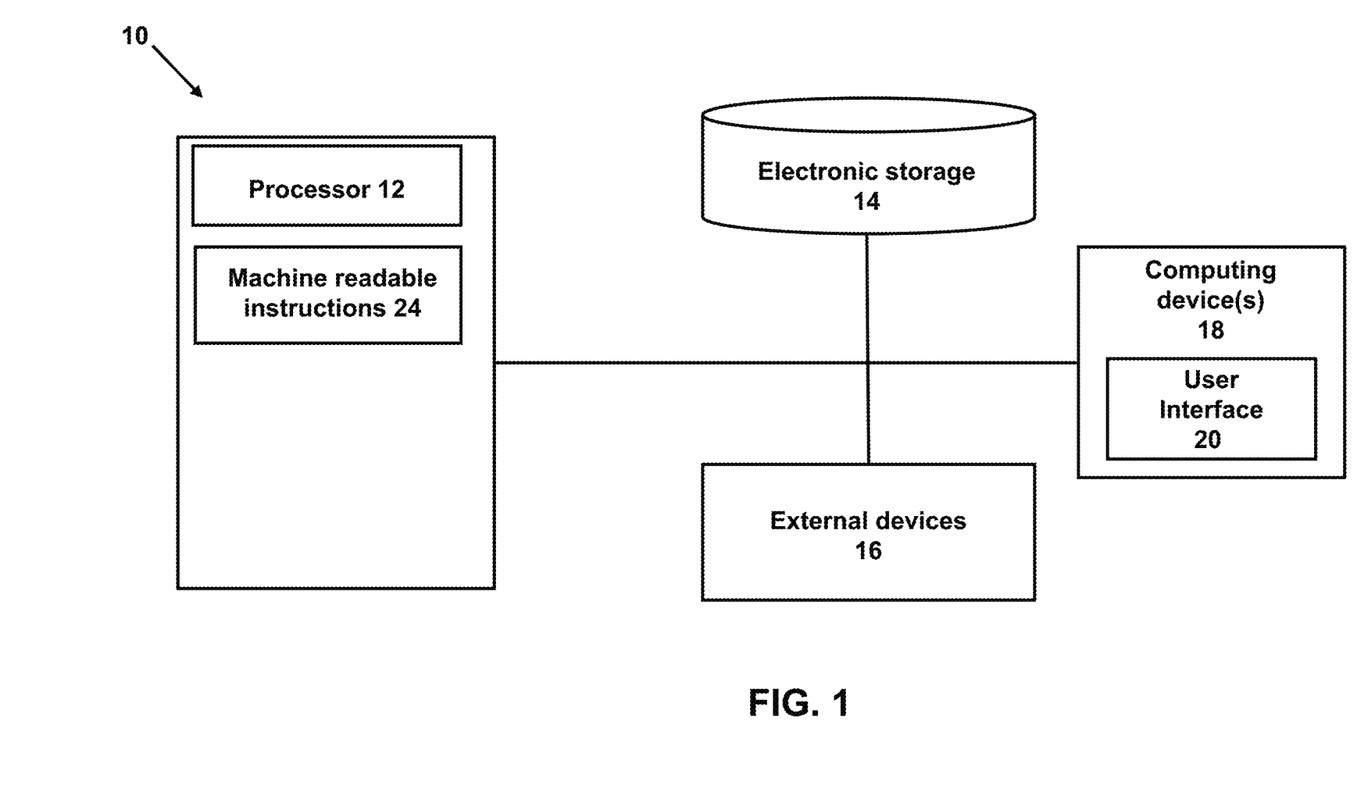
FIG. 1 is a schematic illustration of a system configured for monitoring gas exchange impairment in accordance with one or more embodiments.

FIG. 1 is a schematic illustration of a system 10 configured for monitoring gas exchange in COPD patients, and more particularly monitoring patients in a home health care environment, or other lower levels of care. For example, it may be applicable to residential independent living facilities, assisted living facilities, and/or nursing homes.

In some embodiments, system 10 comprises processors 12, electronic storage 14, external devices 16, computing device 18 having a user interface 20, or other components. The external devices 16 may be, for example, hospital equipment that obtains data on various health states of a patient.

Electronic storage 14 comprises electronic storage media that electronically stores information (e.g., health, demographic, social information associated with individual patients. The electronic storage media of electronic storage 14 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 14 may be (in whole or in part) a separate component within system 10, or electronic storage 14 may be provided (in whole or in part) integrally with one or more other components of system 10 (e.g., computing device 18, etc.). In some embodiments, electronic storage 14 may be located in a server together with processors 12, in a server that is remote from a caregiving location. Electronic storage 14 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 14 may store software algorithms, information determined by processors 12, information received via processors 12 and/or graphical user interface 20 and/or other external computing systems, information received from external devices 16, and/or other information that enables system 10 to function as described herein.

External devices 16 include sources of information and/or other resources. For example, external devices 16 may include monitoring devices including oxygen and ventilation therapy devices, pulse oximeters, activity monitors, sleep monitors, or the like. In some embodiments, external devices 16 include components that facilitate communication of information such as a network (e.g., the internet), electronic storage, equipment related to Wi-Fi technology, equipment related to Bluetooth® technology, data entry devices, sensors, scanners, and/or other resources. In some embodiments, some or all of the functionality attributed herein to external resources 16 may be provided by resources included in system 10.

Processors 12, electronic storage 14, external devices 16, computing device 18, and/or other components of system 10 may be configured to communicate with one another, via wired and/or wireless connections, via a network (e.g., a local area network and/or the internet), via cellular technology, via Wi-Fi technology, and/or via other resources. It will be appreciated that this is not intended to be limiting, and that the scope of this disclosure includes embodiments in which these components may be operatively linked via some other communication media. In some embodiments, processors 12, electronic storage 14, external devices 16, computing device 18, and/or other components of system 10 may be configured to communicate with one another according to a client/server architecture, a peer-to-peer architecture, and/or other architectures.

In embodiments, external devices 16 may include, for example, home monitoring equipment that is either fixed or mobile. It may include a wearable or other user device that monitors heart rate, oxygen saturation, blood pressure, temperature, or other information relevant to the user's health or well being.

Computing device 18 may be configured to provide an interface between one or more users, and system 10. In some embodiments, computing device 18 is and/or is included in desktop computers, laptop computers, tablet computers, smartphones, smart wearable devices including augmented reality devices (e.g., Google Glass), wrist-worn devices (e.g., Apple Watch), and/or other computing devices associated with a user. In some embodiments, computing device 18 facilitates presentation of a list of individuals assigned to a care manager, or other information. Accordingly, computing device 18 comprises a user interface 20. Examples of interface devices suitable for inclusion in user interface 20 include a touch screen, a keypad, touch sensitive or physical buttons, switches, a keyboard, knobs, levers, a camera, a display, speakers, a microphone, an indicator light, an audible alarm, a printer, tactile haptic feedback device, or other interface devices. The present disclosure also contemplates that computing device 18 includes a removable storage interface. In this example, information may be loaded into computing device 18 from removable storage (e.g., a smart card, a flash drive, a removable disk, etc.) that enables caregivers or other users to customize the implementation of computing device 18. Other exemplary input devices and techniques adapted for use with computing device 18 or the user interface include an RS-232 port, RF link, an IR link, a modem (telephone, cable, etc.), or other devices or techniques.

Processor 12 is configured to provide information processing capabilities in system 10. As such, processor 12 may comprise one or more of a digital processor, an analog processor, a digital circuit designed to process information, an analog circuit designed to process information, a state machine, or other mechanisms for electronically processing information. Although processor 12 is shown in FIG. 1 as a single entity, this is for illustrative purposes only. In some embodiments, processor 12 may comprise a plurality of processing units. These processing units may be physically located within the same device (e.g., a server), or processor 12 may represent processing functionality of a plurality of devices operating in coordination (e.g., one or more servers, computing device, devices that are part of external resources 16, electronic storage 14, or other devices.)

As shown in FIG. 1, processor 12 is configured via machine-readable instructions 24 to execute one or more computer program components. The computer program components may comprise one or components for performing steps of a method in accordance with one or more embodiments. Processor 12 may be configured to execute components by software; hardware; firmware; some combination of software, hardware, or firmware; or other mechanisms for configuring processing capabilities on processor 12.

It should be appreciated that although the components are illustrated in FIG. 1 as being co-located within a single processing unit, in embodiments in which processor 12 comprises multiple processing units, one or more components may be located remotely from the other components. The description of the functionality provided by the different components described below is for illustrative purposes, and is not intended to be limiting, as any of components may provide more or less functionality than is described. For example, one or more of the components may be eliminated, and some or all of its functionality may be provided by other components. As another example, processor 12 may be configured to execute one or more additional components that may perform some or all of the functionality attributed below to one of components.

The system is programmed to accept as inputs blood oxygen and/or ventilation data and, using a model, determining physiological dead space and pulmonary shunt information. The resulting information may be reported to a case manager, clinician, or other caregiver for action. In an embodiment, the values are collected periodically and reported as a trend to a caregiver.

In an embodiment, the system 10 detects a desaturation by way of pulse oximetry, for example using an ear or finger worn pulse oximeter. Then, in accordance with the algorithm discussed in more detail below, make a classification of the symptoms to provide a potential diagnosis. That is, in addition to monitoring the COPD progression, in an embodiment, the system may further provide diagnostic information to distinguish underlying sources of impairment and detect comorbid pathologies.

For example, appropriate actions could include modifying therapies or treatments. Ventilation therapy, for example, could be adjusted to reduce effects of the physiological dead space or pulmonary shunt.

Figure 2:
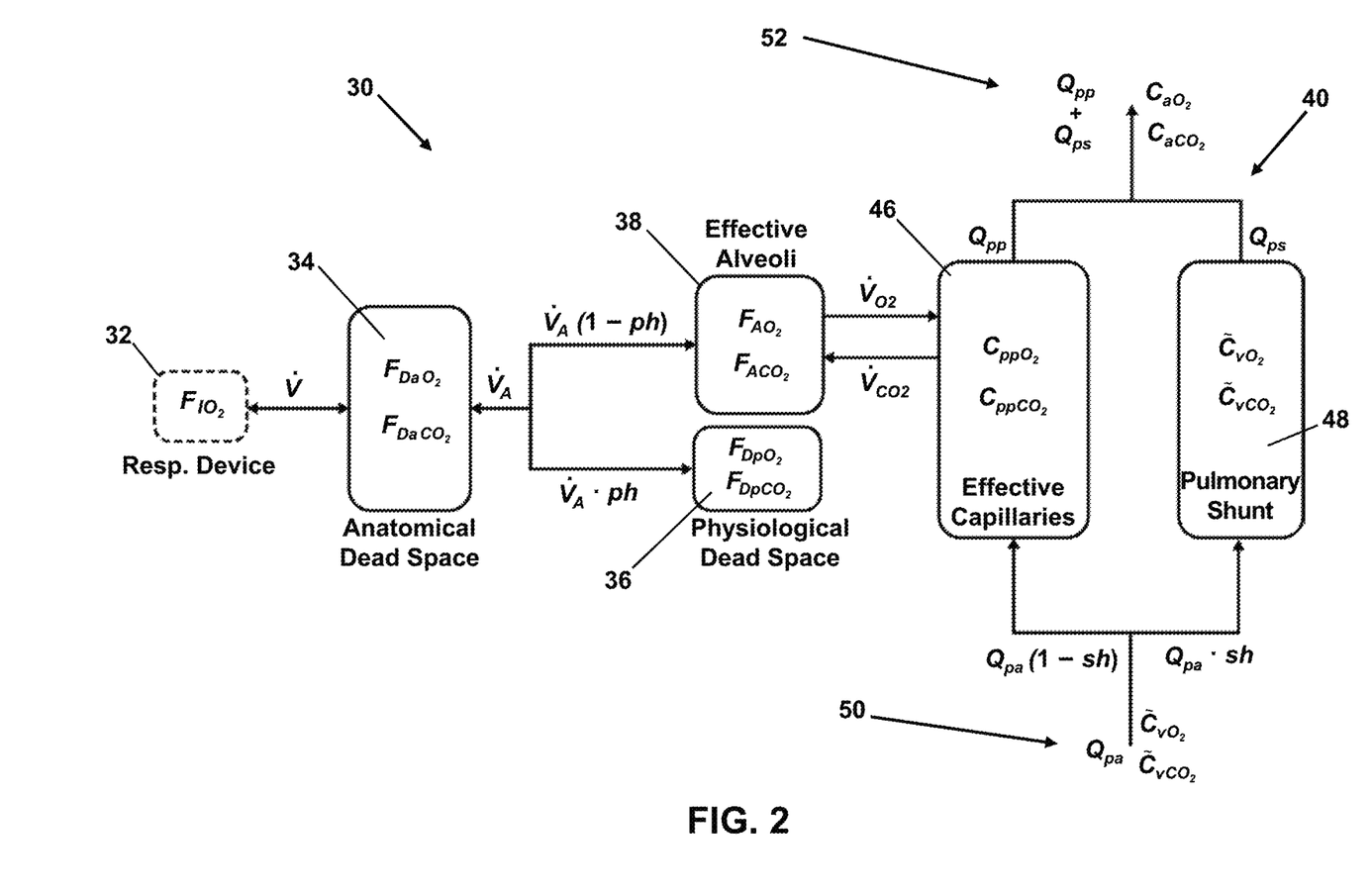
FIG. 2 is a model of the respiratory system, illustrating sources of loss of availability of respiratory volume and oxygen in COPD patients.

FIG. 2 illustrates an example of a model in accordance with an embodiment that relates respiratory 30 and cardiovascular 40 sides of the pulmonary gas exchange process. A respiratory device 32 provides data relating to the ventilation (volume of air in and out) received by the patient from the respiratory device 32. As an example, this device may be a respiratory therapy device such as a CPAP, Bi-PAP, oxygen concentrator, or other breathing support device that is configured to measure ventilation amounts.

As seen in FIG. 2, the total ventilation is first modified by a reduction due to anatomical dead space. Anatomical dead space is defined as that portion of the volume of a breath that is in the pathway to the lungs, but does not play a part in gas exchange. That is, this is the volume of the nose (and/or mouth), trachea, and bronchi. A second fraction is lost due to physiologic dead space 36. This, in COPD patients, is alveolar dead space, or portions of the lungs that are not effectively exchanging gas with blood. Note that some definitions of physiologic dead space includes anatomical dead space. Because a patient's anatomical dead space is essentially constant, the amount of change over time as measured in a patient is generally related to alveolar dead space changes. To the extent that the broader definition is used, this would simply represent a fixed offset to the total model quantifying dead space.

In emphysema, physiological dead space can result from destruction of parenchymal tissue and cell structure at the capillary interface between blood and air in the alveoli. As a result, the lung structure changes to avoid the damaged tissue, which can cause some regions of the lungs to be ventilated but not adequately perfused. Air that reaches these regions is not exchanged efficiently, and some portion of ventilation is lost.

Emphysema may also be comorbid with pulmonary fibrosis or scarring of the lung tissue. This combination is known as combined pulmonary fibrosis and emphysema (CPFE). This condition can be diagnosed by a reduction of lung elasticity, which can, in an embodiment, be determined using mechanical ventilation to measure compliance or elastance by analyzing changes in tidal volume when ventilation pressure is changed.

The remainder of the breathing volume is that portion that is taken into the effective alveoli 38. It is this portion of the volume that is involved in gas exchange. It is represented in the model by the volume $V_A$ (1-ph). That is, the volume adjusted for anatomical dead space times one minus the fraction lost due to physiological dead space.

The effective alveoli 38 exchanges oxygen ($V_{O2}$) for carbon dioxide ($V_{CO2}$) with the effective capillaries 46. In COPD patients, some lung effectiveness is lost to pulmonary shunt. A pulmonary shunt is a condition in which alveoli are appropriately fed by capillaries with blood, but they are not receiving appropriate air supply. This is represented in the Figure by showing that the pulmonary shunt fraction 48 is not in gas exchange communication with the effective alveoli.

In chronic bronchitis, for example, some small airways are blocked by inflammation, mucous, collapse, inability of damaged cilia to remove secretions, or a combination of these factors. As a result, the capillary beds of alveoli are perfused, but not adequately ventilated. Wasted perfusion reduces gas exchange efficiency.

In an embodiment, pulmonary hypertension effects may also be taken into account. In pulmonary hypertension, stress on the pulmonary arteries may result from changes to vascular pathways. Additionally vasoconstriction as a result of hypoxemia and inflammation are often present, resulting in increased pulmonary resistance, increased pulmonary artery pressure, and potentially heart failure.

As shown in the Figure, the model takes into account flow of blood in the pulmonary artery $Q_{pa}$, as well as the venous concentrations 50 of oxygen and carbon dioxide $C_{vO2}$ and $C_{vCO2}$. Likewise, the arterial concentrations 52 of oxygen and carbon dioxide on an output side $C_{aO2}$ and $C_{acO2}$ are taken into account.

By monitoring $SP_{O2}$ and breath rate, then, it is possible to determine what physiological dead space fraction 36 and the shunt fraction 48 may be determined.

Pulmonary embolism may also be present as a result of arterial hypoxemia. In pulmonary embolism, a pulmonary artery may be blocked resulting in dead space and insufficient perfusion. As in other conditions with reduced perfusion, some ventilation becomes wasted and gas exchange is impaired.

In ARDS (Acute Respiratory Distress Syndrome), there is a rapid onset of widespread inflammation in the lungs, which increases permeability of the membranes, allowing fluid to enter alveoli. This results in poor perfusion and can lead to persistent arterial hypoxemia.

Hypoxemia may occur transiently during sleep due to hypoventilation during REM sleep. Another possible source of transient hypoxemia is obstructive sleep apnea (OSA). Up to 40% of COPD patients show symptoms of OSA resulting in oxygen saturation reductions of up to 10%, even with very short apnea periods. The system may detect transient hypoxemia, as desaturations occur and disappear and then review the history of ventilator data to determine if the transient hypoxemic event (THE) is a result of hypopnea, due to apnea or due to some non-specific reason that could include build up of mucus, or perhaps a loose fitting of the probe on the finger.

Figure 3:
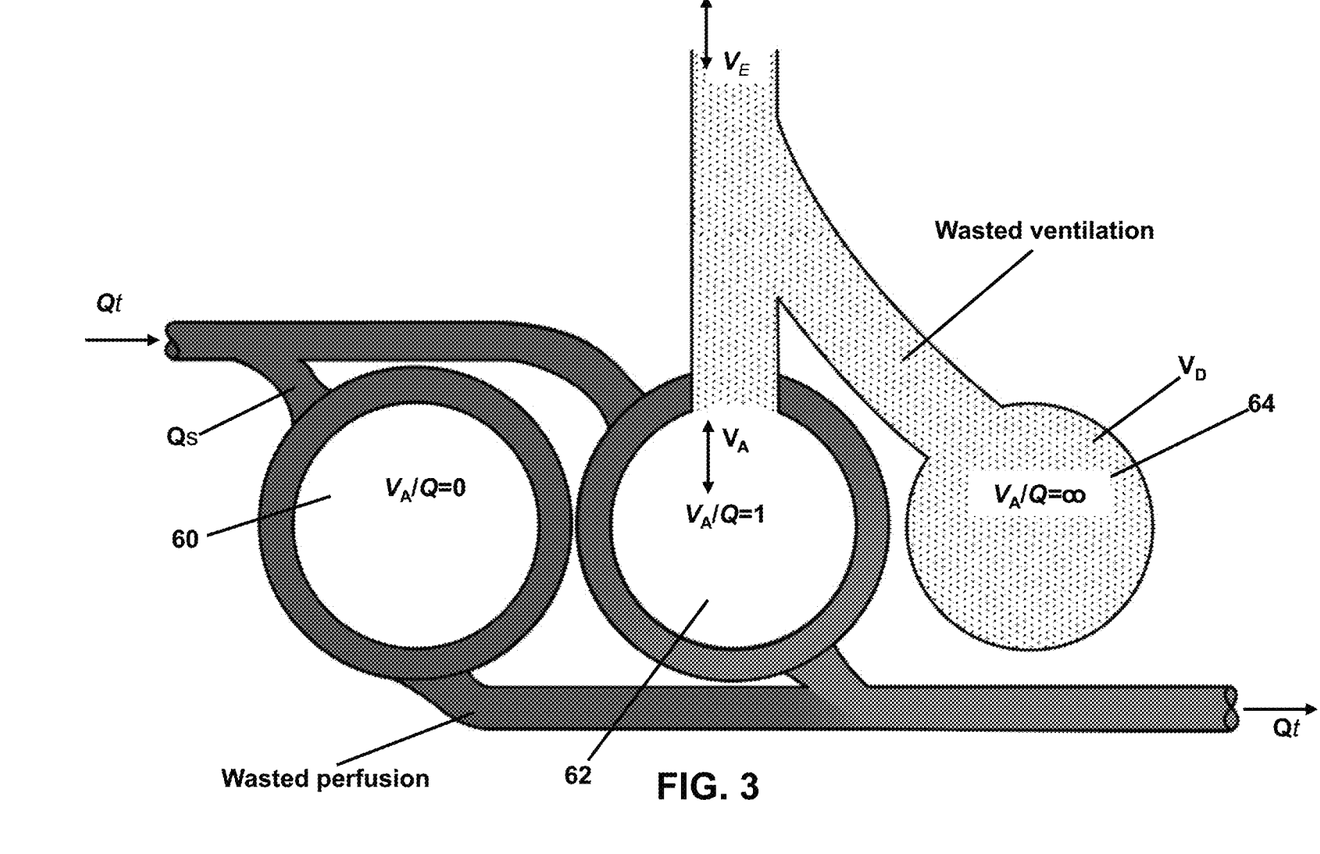
FIG. 3 is a simplified model of the respiratory system illustrating cases of wasted perfusion, wasted ventilation, and ordinary exchange.

FIG. 3 schematically illustrates a model of ventilation and respiration in accordance with an embodiment. In the Figure, there are three regions 60, 62, 64, representing different portions of a lung/artery system. Each region broadly represents portions of the system that are working at different efficiencies. For the purposes of illustration, they are selected to be extreme values. In an actual lung, there will be generally be variations and gradations.

FIG. 3 shows ventilation/perfusion ratios ($V_A/Q$), which is a ratio that is typically used to assess the efficiency and adequacy of the matching between the air that reaches the alveoli (alveolar ventilation, or ventilation, $V_A$) and the blood that reaches the alveoli via the capillaries (perfusion, Q). In region 60, the ratio is zero, indicating that there is no ventilation, such that despite good perfusion, that perfusion is wasted. This represents a portion of the lung affected by shunt. Region 62 is one that is well-perfused and well ventilated, so the ratio is 1, indicating good gas exchange. This represents a healthy portion of a lung system. Finally, region 64 is one that is well ventilated and poorly perfused, resulting in a ratio that is infinite and could be, for example, a portion of the lung affected by emphysema.

As noted above, shunt is the fraction of deoxygenated mixed venous blood that passes from the right to the left heart without participating in gas exchange; that is, shunt results in wasted perfusion ($V_A/Q=0$). Shunt in its most general definition comprises two main components: 1) The anatomic shunt (absolute or true shunt) that completely bypasses the alveoli and includes the normal shunts due to the bronchial, pleural, and the besian veins (typically about 1-2% of cardiac output) and the abnormal shunts caused by alveolar fluid accumulation, consolidation, and collapse; and 2) Shunt-like effects that involve ventilation-perfusion mismatch, i.e., more perfusion than ventilation that causes less than 100% hemoglobin saturation.

To measure shunt, it is useful to ensure that arterial and mixed venous blood samples are taken more or less simultaneously. In this case, simultaneous can be considered to be measurements within a same respiratory cycle (i.e. during the same breath). Blood samples are analyzed to measure the partial pressure of oxygen ($P_{O2}$) and the saturation of oxygen ($S_{O2}$). Alternately, $PO_2$ may be measured using a $P_{O2}$ electrode Oxygen concentration in arterial ($CA_{O2}$) and in mixed venous blood ($C_{VO2}$) can then be computed from the measured $P_{O2}$ and $S_{O2}$. The shunt fraction then can be calculated in accordance with equation (1).

$$\frac{Q_s}{Q_t} = \frac{Cc'O_2 - CaO_2}{Cc'O_2 - C\bar{v}O_2} \qquad (1)$$

wherein $Q_t$ is the total blood flow (cardiac output), $Q_s$ is the blood flow through the shunt, $Cc'O_2$ is the $O_2$ concentration of end-capillary blood, which is usually calculated from the alveolar Poe and the oxygen dissociation curve. This method and other methods typically require drawing blood from the patient and also generally require the use of expensive gas analyzers.

As described above, dead space relates to a volume of air that is inhaled but does not participate in the gas exchange; that is, dead space results in wasted ventilation ($V_A/A=\infty$), region 64. The total dead space (physiological) comprises the volume of air that remains in the conducting airways (anatomic dead space) and the volume of air that reaches those alveoli that are not perfused or are poorly perfused (alveolar dead space or dead space-like effects). Computation of the dead space is done by employing the mass balance in the expired gas in accordance with equation (2):

$$\frac{V_d}{V_t} = \frac{(PaCO_2 - PeCO_2)}{PaCO_2} \qquad (2)$$

wherein $V_d$ is the dead space volume, $V_t$ is the tidal volume, $Pa_{CO2}$ is the partial pressure of carbon dioxide ($CO_2$) in the arterial blood, and $PeCO_2$ is the partial pressure of $CO_2$ in the expired air.

If $PeCO_2$ is replaced by the mixed expired $CO_2$, then the above equation (2) gives the physiological dead space, whereas if $PeCO_2$ is placed by the end-tidal $CO_2$ then it produces the alveolar dead space.

To perform the necessary measurements, the system 10 includes the external resources 16. These may include, in embodiments, one or more of therapeutic devices for ventilation therapy, pulse-oximeters, $CO_2$ monitoring devices such as transcutaneous $CO_2$ monitors, activity monitors, and sleep monitors. In embodiments, one of each type of device may be present, or some combination of devices may be present. The external resources 16 may be connected wirelessly or with a wired connection to the system 10. Data from the external resources 16 are provided as input(s) to the processor 12 so that they can be processed in accordance with the machine readable and executable instructions 24.

In an embodiment, an algorithm uses oxygen, carbon dioxide, and/or ventilation data as primary inputs, plus vital signs, activity, and sleep data to control for confounding factors that also affect pulse-oximetry and $CO_2$ measurements. The system collects data and analyzes them (locally or remotely) as explained below.

A variety of measurements can be made using the external resources 16 including one or more of the following values:

$SpO_2$ is the peripheral capillary oxygen saturation, an estimate of the amount of oxygen in the blood. More specifically, it is the percentage of oxygenated hemoglobin (hemoglobin containing oxygen) compared to the total amount of hemoglobin in the blood (oxygenated and non-oxygenated hemoglobin). This may be measured, for example, using an ear or finger worn pulse oximeter.

$SpO_2$ response is a measurement characterizing the rate of change of oxygen saturation (as read by a pulse oximeter) following the initiation of pure oxygen therapy. This is known as flush therapy (Flush=100% $FiO_2$—Fraction of inhaled oxygen) in which the pure oxygen flushes out nitrogen from the respiratory system. The $SpO_2$ can be expressed in the following ways:

Time Response: Time required for $SpO_2$ to reach 90% of the final value after the initiation of 100% $FiO_2$.

Time Constant: Time required for $SpO_2$ to reach 63% of the final value after the initiation of 100% $FiO_2$.

Breath Response: Number of breaths required for $SpO_2$ to reach 90% of the final value after the initiation of 100% $FiO_2$.

Volume Response: The total ventilation (Tidal Volume * n breaths) required for $SpO_2$ to reach 90% of the final value after the initiation of 100% $FiO_2$.

$EtCO_2$ is the partial pressure of carbon dioxide at end of each breath cycle (end-tidal $CO_2$) and it is typically assessed via waveform capnography. $EtCO_2$ is considered to be a close proxy of alveolar $CO_2$ levels.

$tcpCO_2$ is a measurement of the $CO_2$ partial pressure of the skin, which in an embodiment is able to provide a continuous indirect estimation of arterial $CO_2$ partial pressure.

$FiO_2$ is the fraction of oxygen in the inspired air. Ambient air has $FiO_2$ equal to 21%, but mechanically ventilated patients can be administered with oxygen levels up to 100%. In this regard, a ventilator may include a blender, a device that is able to blend pure oxygen with air to produce a selected fraction of inhaled oxygen.

Other factors that may be useful in application of a method in accordance with an embodiment include estimates of respiratory system mechanical properties including resistance ($R_{rs}$) and elastance ($E_{rs}$). Such measurements may be made, for example, by measuring changes in tidal volume as pressure in the breathing support is changed. Additional events of interest may include: sleep apnea events (no breathing) of 10 seconds or more, reductions of 90% or more of inspired flow for 10 seconds or more, abnormal or shallow breathing, if inspired flow drops by more than 30% but less than 90% for 10 seconds or more, a drop in oxygen saturation (for example, 3% or more), and Cheyne-Stokes respiration (a pattern of brief apnea followed by fast deep breathing).

To detect Cheyne-Stokes respiration events, there are a variety of available methods include not limited to state machines, frequency information calculated from wavelets, machine learning classifiers on epochs of respiratory flow and oximetry data. A useful definition of CSR is a pattern of breathing in which there is at least one apnea of 10 seconds or more, followed by a period of hyperventilation, and an overall cycle time of 30-120 seconds.

Progression of COPD is characterized by increases in the number of poorly ventilated alveoli having $V_A/Q \ll 1$. This results in shunt-like effects in which perfusion may be adequate but ventilation is poor. This is illustrated schematically in FIG. 4.

Figure 4:
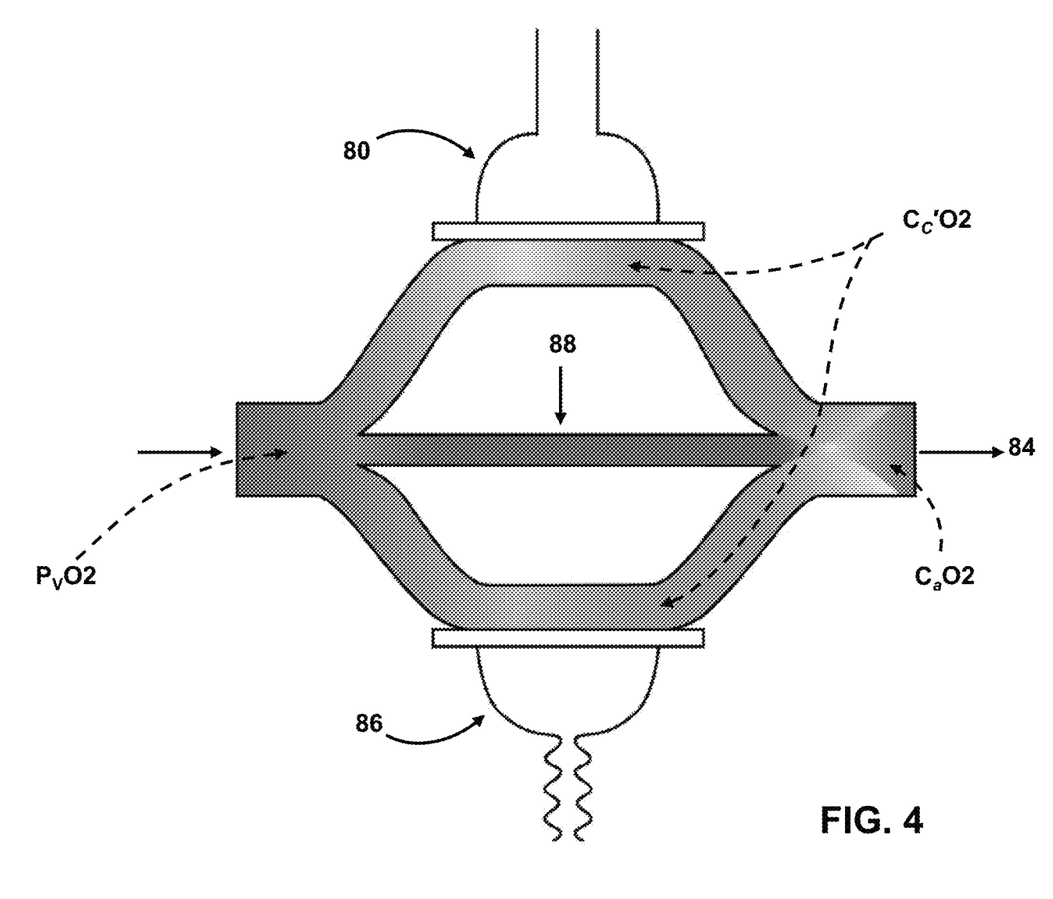
FIG. 4 is a schematic illustration of poorly ventilated alveoli leading to shunt-like effects.

A well-ventilated alveolar unit 80 exchanges gas with blood from the pulmonary artery 82 and passes on oxygenated blood with an oxygenation Cc' $O_2$ to the pulmonary vein 84 while the poorly-ventilated alveolar unit 86 does not receive as much oxygen due to the shunt-like effects. For the purpose of illustration, an anatomical shunt 88 is also illustrated.

For the poorly ventilated alveoli, flush therapy as described above will require a relatively longer measured time response. This is because nitrogen ($N_2$) will take longer to be flushed from the poorly ventilated alveoli. In ordinary air, $N_2$ occupies 79% of ambient air which has approximately 21% $FiO_2$. When alveolar oxygen concentration reaches 100%, then it can be said that the air has been completely displaced by the flushing $O_2$.

Figure 5:
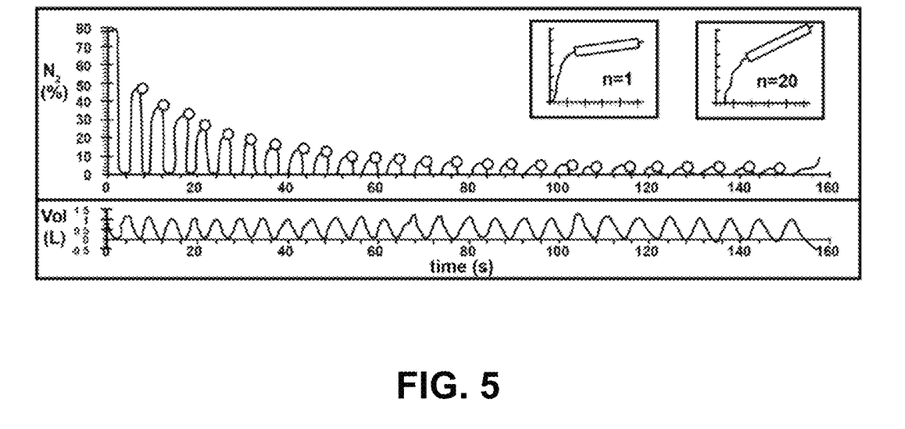
FIG. 5 illustrates decreasing nitrogen saturation during a multiple breath nitrogen washout test.
Figure 6:
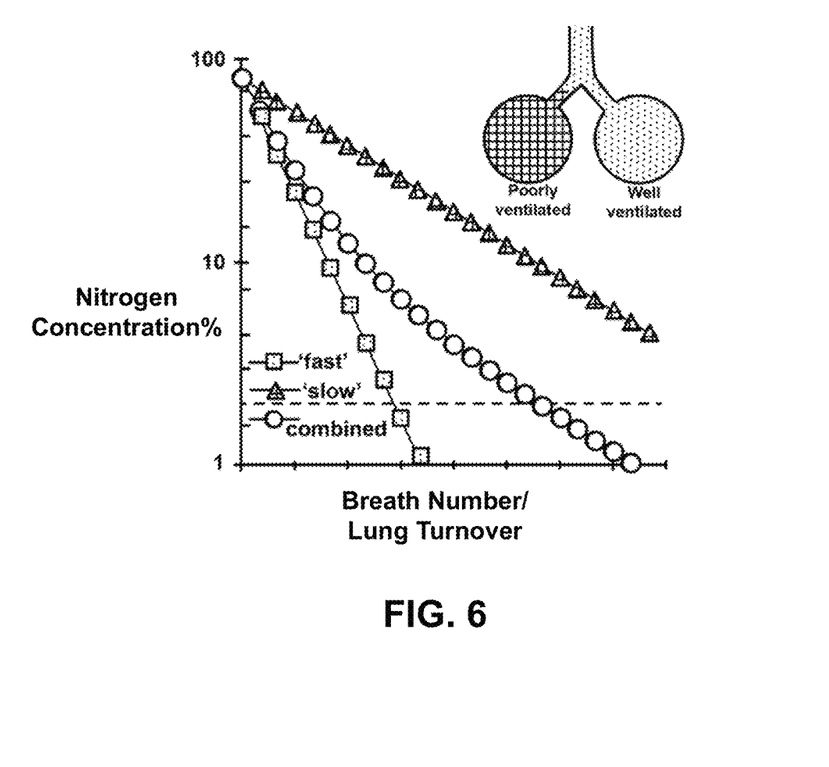
FIG. 6 illustrates decreasing nitrogen saturation in well-ventilated alveoli, poorly-vented alveoli, and the combination during a simulated multiple breath nitrogen washout test.

The multiple-breath nitrogen washout (MBNW) test is a test to quantify the time required for nitrogen to washout from the lung. It is performed by administering 100% $FiO_2$ and measuring the $N_2$ concentration in the expired air. FIGS. 4 and 5 illustrate an example of simulated data from an MBNW test. FIG. 4 generally illustrates the progressive reduction in $N_2$ concentration over a series of breaths during an MBNW test. While FIG. 5 illustrates of a number of breaths required for the $N_2$ to be flushed during a test, particularly illustrating the differences between poorly ventilated and well-ventilated alveolar units. FIG. 5 compares the rate of decrease between well ventilated alveoli (squares) and poorly ventilated alveoli (triangles), plotted on a logarithmic scale. The circles represent an overall rate of decrease for a combined system including both well and poorly ventilated alveoli.

Figure 7:
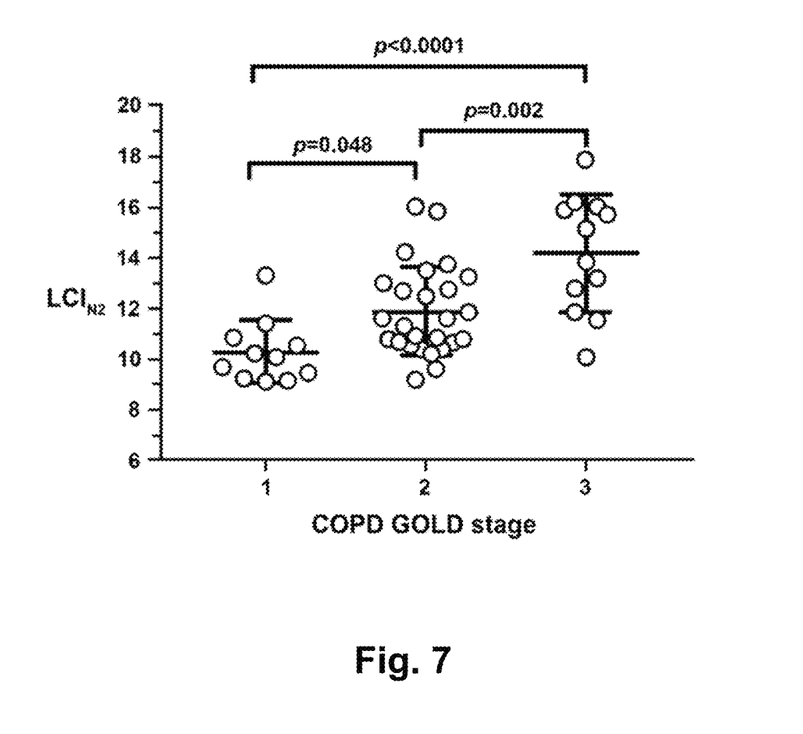
FIG. 7 plots lung clearance index against COPD severity on the GOLD staging system.

Therefore, a higher number of poorly ventilated alveolar units as the result of a worsening COPD condition and the corresponding progressive gas exchange impairment should tend to result in slower nitrogen washout. That is, in a MBNW test, there should be a slower decrease in nitrogen and corresponding slower increase in increase in the alveolar oxygen concentration in response to a step increase in $FiO_2$ to 100%. This characteristically slower response can be seen in FIG. 8 for two patients in different GOLD stages of COPD (Should the note say GOLD stage 2 and not 3). In FIG. 7, the lung clearance index ($LCI_{N2}$) is related to different groups of COPD patients in accordance with their GOLD stage (1, 2, 3). As can be seen, higher GOLD stage is associated with higher $LCI_{N2}$ (i.e., longer time to clear).

Figure 8:
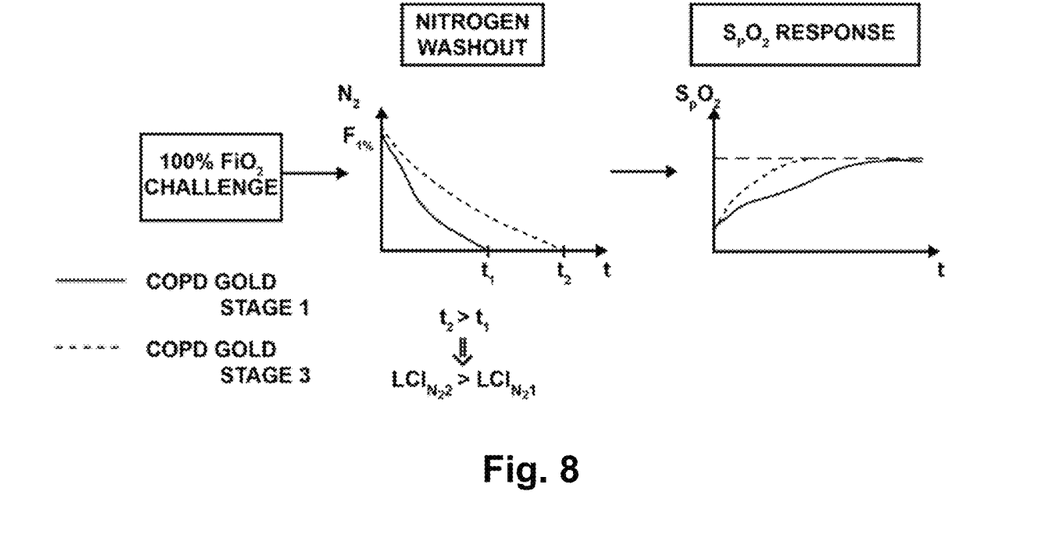
FIG. 8 illustrates theoretical responses to nitrogen flushing for patients in different GOLD stages.

For a patient who has constant anatomical shunt, any change in the alveolar oxygen concentration due to a change in $FiO_2$ should be transmitted to the arteries. Arterial oxygen content may be quantified via the arterial oxygen saturation level ($SaO_2$). $SpO_2$, which may be measured using a finger worn device, for example, is a proxy of $SaO_2$. Thus, it is reasonable to expect that the time response of $SpO_2$ after $FiO_2$ is increased to 100% will be longer ($SpO_2$ will reach its final value at a slower pace) if there is gas exchange impairment (more poorly ventilated alveoli and slower nitrogen washout) due to worsening COPD conditions. FIG. 8 shows a sample comparative illustration of the expected responses to the 100% $FiO_2$ challenge of two different COPD GOLD stages.

Figure 9:
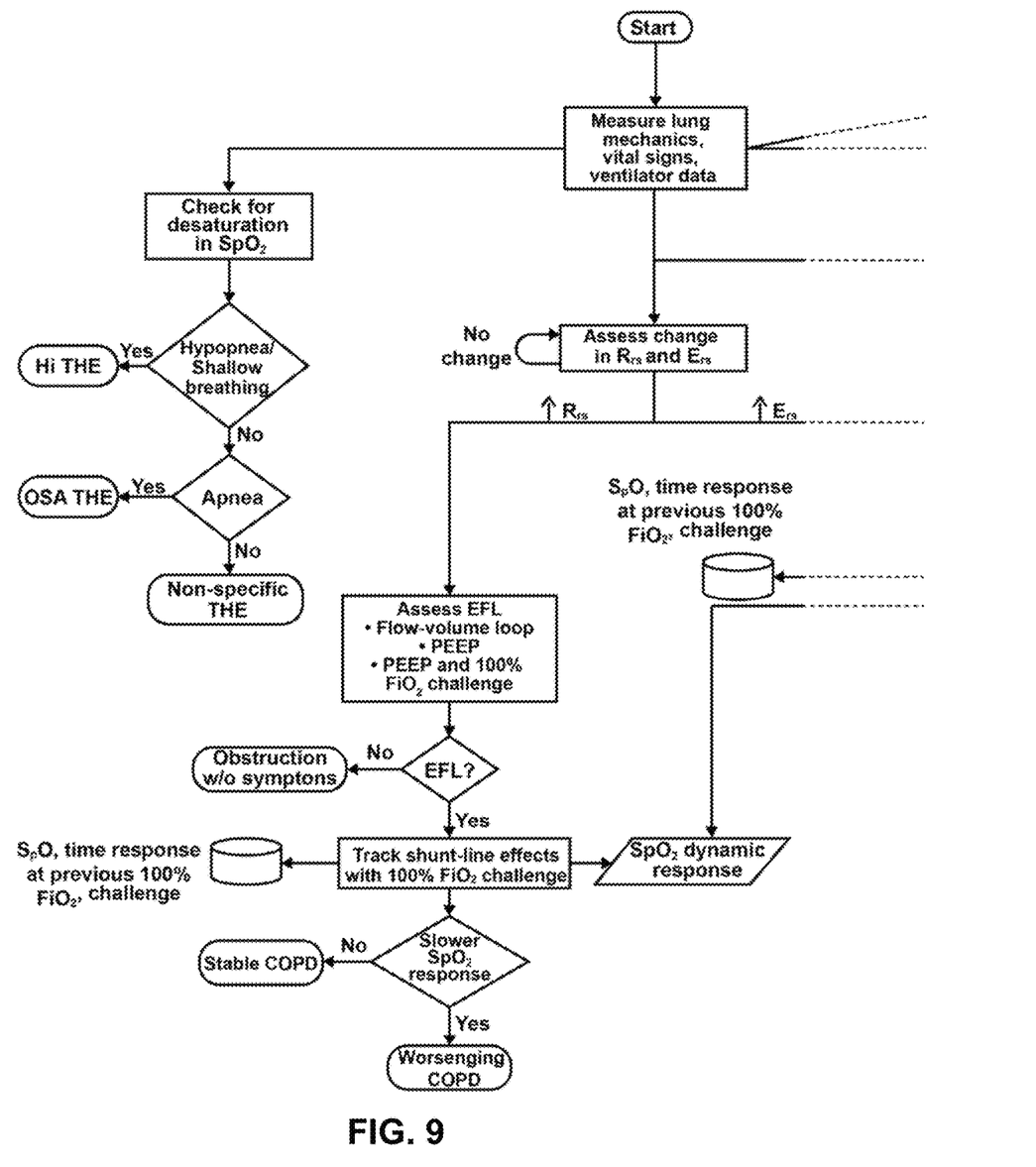
FIG. 9 is a flowchart in accordance with an embodiment.

In an embodiment, the system proceeds in accordance with a decision tree by which a classification of a detected impairment may be determined. As described above, impairments may be linked to one or both of wasted ventilation (dead space) or wasted perfusion (shunt). FIG. 9 shows one possible decision tree to discriminate between different disease episodes assuming that the prescription of mechanical ventilation support is due to a COPD condition. FIG. 9 illustrates branching decisions based on the results of each test, and indicating which possible additional tests may be used to proceed to the next level of identification of the source of the impairment. The decision tree reads as follows:

To assess the baseline conditions, the ventilator may 1) estimate a respiratory system resistance ($R_{rs}$) and elastance ($E_{rs}$) and 2) measure the $SpO_2$ response to a 100% $FiO_2$ challenge. The ventilator may then continuously monitor $R_{rs}$ and $E_{rs}$ values. Ventilators that include such continuous monitoring functionality include, for example, Trinity ventilators available from Philips Healthcare.

In an embodiment, the system may make use of ventilation data (such as tidal volume, patient flow, applied airway pressure and respiratory rate) plus vital signs (e.g., heart rate), activity, and sleep data to control for confounding factors (such as exercise and increased metabolic demands) that affect gas exchange and hence pulse-oximetry and $CO_2$ measurements.

If an increased in $R_{rs}$ is detected by detecting a greater resistance to flow changes when pressure is applied by the ventilator, the ventilator may trigger a test to assess the presence of expiratory flow limitation (EFL). Such a test can include, but is not limited to, flow-volume loops, estimation of intrinsic PEEP ($PEEP_i$) (positive-end expiratory pressure) as an indicator of hyperinflation. Or the system may imply that EFL exists by administering a PEEP treatment and observe that EFL is abolished by PEEP. Or the machine may administer a combination of PEEP titration with the 100% $FiO_2$ challenge. PEEP acts to mitigate the effects of EFL, which should therefore, when applied in combination with the 100% $FiO_2$ challenge, lead to an improved $SpO_2$ response to the 100% $FiO_2$ challenge. That is, if improved (i.e., faster) $SpO_2$ response is observed during this test, then EFL may be determined to be the cause of the observed impairment.

If EFL is detected, the increase in $R_{rs}$ may be attributed to a worsening COPD condition such as a potential exacerbation episode or bronchospasm. The ventilator may also use the 100% $FiO_2$ challenge (with no PEEP increase) to quantify the shunt-like effects as part of a potential progressive impairment of gas exchange in COPD, as described previously.

In the case that EFL is not detected, then the increase in $R_{rs}$ is attributed to obstruction without symptoms, such as secretion accumulation.

If no significant increase in resistance is found compared to baseline, but an increase in $E_{rs}$ is detected, the machine may perform a PEEP titration and 100% $FiO_2$ challenge combo test to classify the worsening condition as either of ARDS-type or lung fibrosis. Because PEEP tends to improve gas exchange in ARDS patients, there should be an observed improvement in $SpO_2$ response to the 100% $FiO_2$ challenge. On the other hand, lung fibrosis is not expected to demonstrate improved gas exchange after PEEP application, thus this test may distinguish those two conditions.

If no changes in $R_{rs}$ or $E_{rs}$ are detected, the ventilator may check for one or more of the following signs: hyperventilation, increased $EtCO_2$-$tcpPCO_2$ difference as proxy of increase in wasted ventilation (deadspace), and/or change in final value of $SpO_2$ for 100% $FiO_2$. If a combination of these signs is found, the test may make a determination that pulmonary embolism is the underlying cause.

As will be appreciated, the decision tree of FIG. 9 is not necessarily a binary or deterministic tree. Fuzzy classifiers may be used, or probabilistic decisions may be made at each node or some but not all nodes. Quantitative data over time may be collected and machine learning techniques may be applied including, for example, random forest with boosting and bagging techniques, which may be supervised by expert clinical diagnosis or supplemental measurements made in clinical settings.

In an embodiment, the path along the decision tree may be determined based on a parameter having a highest significance and/or a highest confidence.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system for monitoring lung disease in a patient comprising:
   a ventilation therapy device, configured to provide ventilation therapy to the patient and to determine tidal volumes, flow of gas, and applied pressure provided to the patient, the ventilation therapy device including a blender configured and arranged to control a fraction of inhaled oxygen to perform a nitrogen washout test;
   an oxygen saturation monitor, configured to determine a saturation of oxygen in the patient's blood;
   a processor configured by machine-readable instructions to:
   control the ventilation therapy device to perform the nitrogen washout test;
   determine, based on a result of the nitrogen washout test and the determined saturation of oxygen in the patient's blood, a change in gas exchange impairment in the patient; and
   determine, based at least in part on the result of the nitrogen washout test and the determined saturation of oxygen in the patient's blood, a cause of the change in gas exchange impairment in the patient.

2. The system of claim 1, wherein the ventilation therapy device is further configured to estimate a lung elastance, and wherein the processor is configured to determine the cause of the change in gas exchange impairment in the patient based at least in part on the lung elastance.

3. The system of claim 1, wherein the ventilation therapy device is further configured to administer positive-end expiratory pressure in conjunction with the nitrogen washout and wherein the processor is further configured to distinguish acute respiratory distress syndrome from pulmonary fibrosis on the basis of a time response of the saturation of oxygen in the patient's blood when the positive-end expiratory pressure is administered in conjunction with the nitrogen washout.

4. The system of claim 1, wherein the processor is further configured to, based on the determined change in gas exchange impairment in the patient, determine a risk for exacerbation and/or re-hospitalization.

5. The system of claim 1, wherein the processor is configured to determine the cause of the change in gas exchange impairment on the basis of a decision tree.

6. The system of claim 5, wherein the processor is further configured to control the system to, in response to one or more nodes of the decision tree, execute additional tests and to use the results of the additional tests to proceed with evaluating the decision tree.

7. The system of claim 6, wherein the additional tests include one or more tests selected from the group consisting of: heart rate, activity, sleep data, expiratory flow limitation tests, oxygen flush challenge tests, hyperventilation, and increased end-tidal $CO_2$, $tcpPCO_2$ difference.

8. A method of monitoring lung disease in a patient comprising:
providing ventilation therapy using a ventilation therapy device to the patient;
determining tidal volumes, flow of gas, and applied pressure provided to the patient using the ventilation therapy device;
determining a saturation of oxygen in the patient's blood;
controlling the ventilation therapy device to perform a nitrogen washout test;
determining, based on a result of the nitrogen washout test and the determined saturation of oxygen in the patient's blood, a change in gas exchange impairment in the patient; and
determining, based at least in part on the result of the nitrogen washout test and the determined saturation of oxygen in the patient's blood, a cause of the change in gas exchange impairment in the patient.

9. The method of claim 8, further comprising:
estimating a lung elastance using the ventilation therapy device; and
determining the cause of the change in gas exchange impairment in the patient based at least in part on the lung elastance.

10. The method of claim 8, further comprising:
administering positive-end expiratory pressure using the ventilation device in conjunction with the nitrogen washout; and
distinguishing acute respiratory distress syndrome from pulmonary fibrosis on the basis of a time response of the saturation of oxygen in the patient's blood when the positive-end expiratory pressure is administered in conjunction with the nitrogen washout.

11. The method of claim 8, further comprising:
administering positive-end expiratory pressure using the ventilation device in conjunction with the nitrogen washout; and
tracking shunt-like effects as indicators of COPD disease progression on the basis of a time response of the saturation of oxygen in the patient's blood when the positive-end expiratory pressure is administered in conjunction with the nitrogen washout.

12. The method of claim 8, further comprising, determining a risk for exacerbation and/or re-hospitalization based on the determined change in gas exchange impairment in the patient.

13. The method of claim 8, wherein determining the cause of the change in gas exchange impairment is performed on the basis of a decision tree.

14. The method of claim 13, further comprising, in response to one or more nodes of the decision tree, executing additional tests using the ventilation therapy device and using the results of the additional tests to proceed with evaluating the decision tree.

15. The method of claim 14, wherein the additional tests include one or more tests selected from the group consisting of: heart rate, activity, sleep data, expiratory flow limitation tests, oxygen flush challenge tests, hyperventilation, and increased end-tidal $CO_2$, $tcpPCO_2$ difference.

* * * * *